United States Patent [19]

Pappas et al.

[11] Patent Number: 4,624,674
[45] Date of Patent: Nov. 25, 1986

[54] SPHERICAL KINEMATIC JOINT

[76] Inventors: Michael J. Pappas, 61 Gould Pl., Caldwell, N.J. 07006; Frederick F. Buechel, 76 Crest Dr., South Orange, N.J. 07079

[21] Appl. No.: 656,507

[22] Filed: Oct. 1, 1984

Related U.S. Application Data

[62] Division of Ser. No. 351,760, Feb. 24, 1982.

[51] Int. Cl.⁴ .............................................. A61F 1/04
[52] U.S. Cl. ..................................................... 623/22
[58] Field of Search ..................... 16/227, 234; 3/1.91, 3/1.912, 1.913; 128/92 S, 92 CA; 403/137, 140

[56] References Cited

U.S. PATENT DOCUMENTS

| | | | |
|---|---|---|---|
| 3,863,273 | 2/1975 | Averell | 3/1.912 |
| 4,044,403 | 8/1977 | Derrico | 3/1.913 |
| 4,135,517 | 1/1979 | Reale | 3/1.91 |

FOREIGN PATENT DOCUMENTS 2052620  1/1981  Fed. Rep. of Germany ......... 3/1.91
1362187  7/1974  United Kingdom ................... 3/1.91

Primary Examiner—Richard J. Apley
Assistant Examiner—David J. Isabella
Attorney, Agent, or Firm—R. Gale Rhodes, Jr.

[57] ABSTRACT

An improved spherical kinematic joint which allows ease and convenience of assembly and disassembly, particularly assembly, by providing a plurality of substantially physically distinct bearing inserts in a subassembly such that the bearing inserts are effectively a unitary structure for the purpose of assembly and disassembly but which bearing segments expand easily with low manual force during assembly and disassembly of the various bearing insert embodiments from the head and/or cavity or spherical seat in another joint element or member, such as for example in the prosthetic joint embodiments, an acetabular cup. Further, such ease of assembly and disassembly can be accomplished while retaining great dislocation and separation resistance and can be accomplished in a manner which does not introduce significant axial play.

18 Claims, 34 Drawing Figures

IMPROVED PROSTHETIC HIP JOINT IMPLANTED

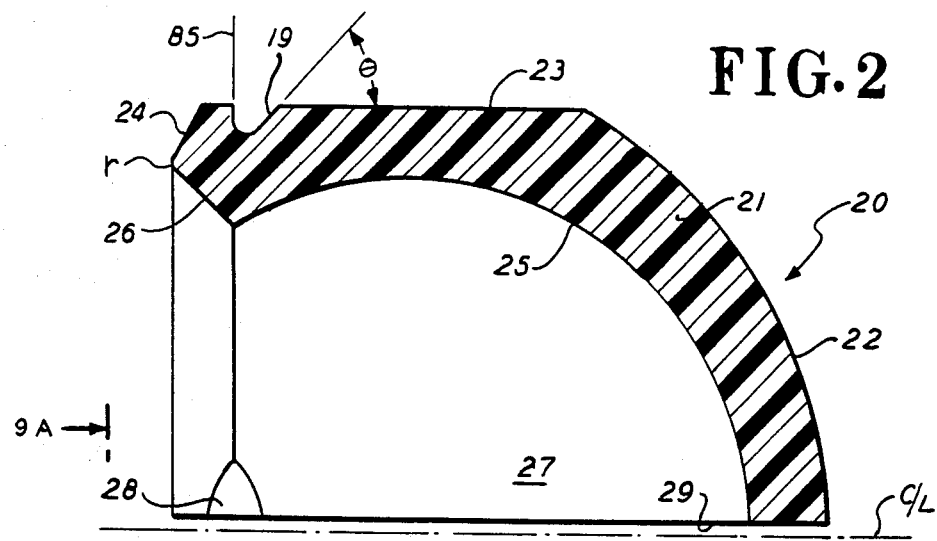
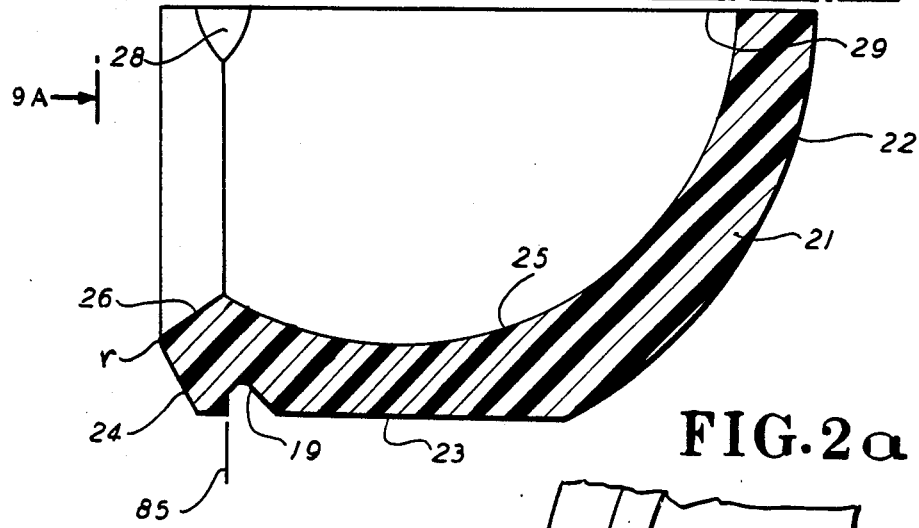
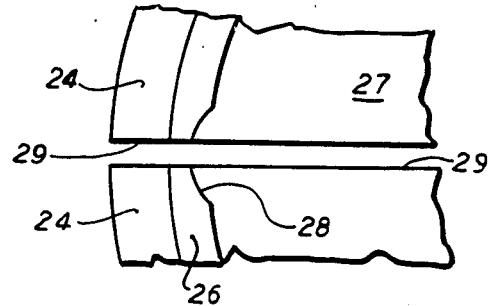
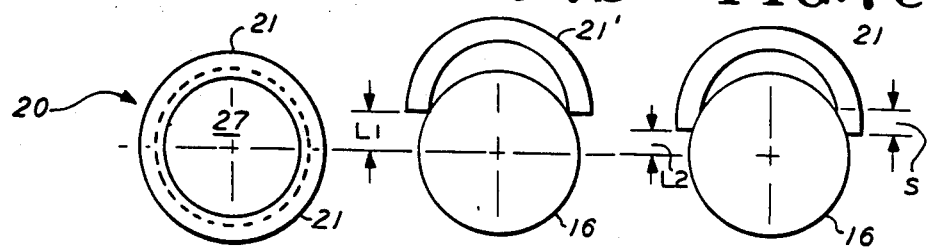

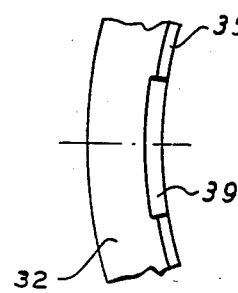
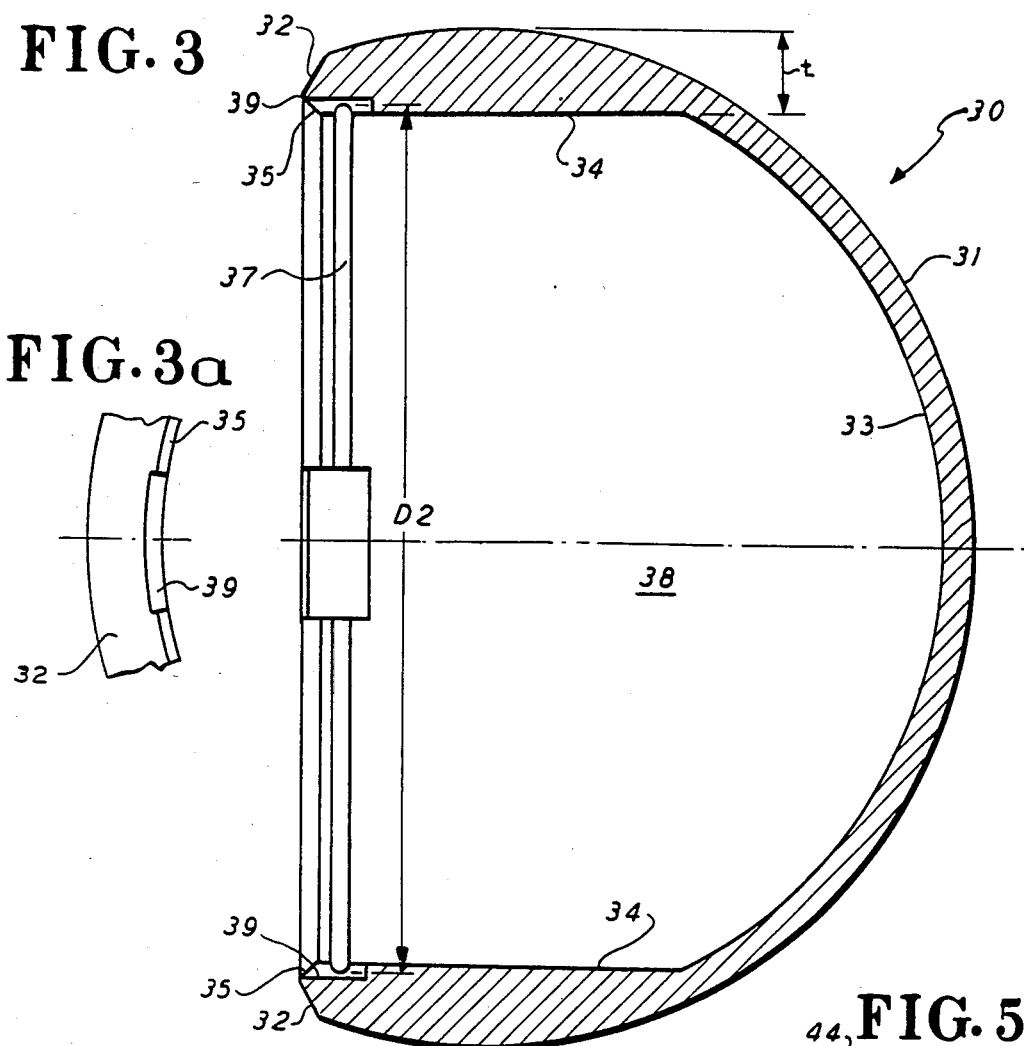
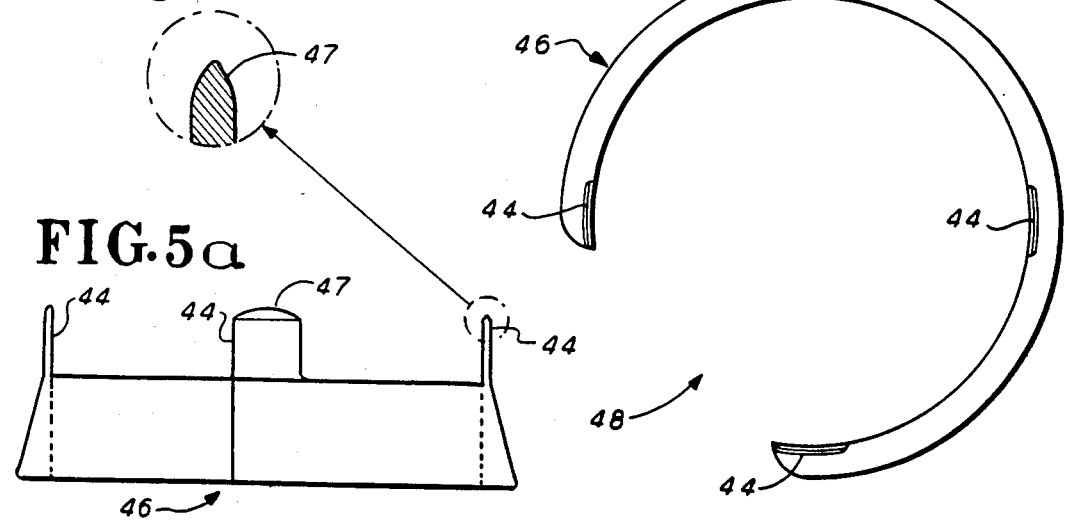

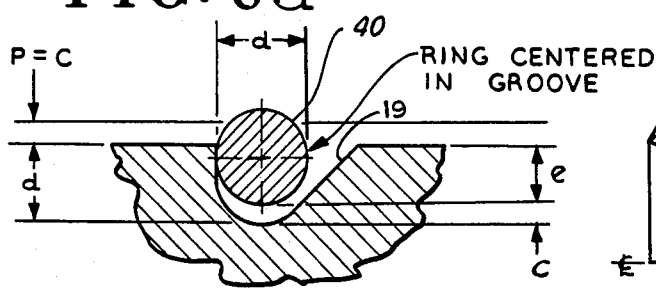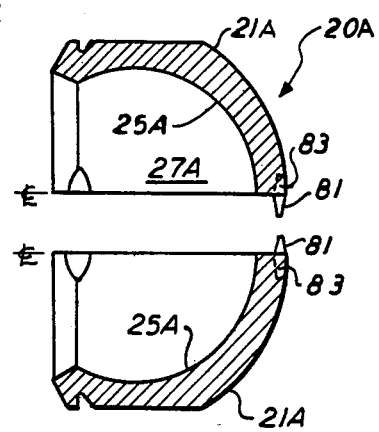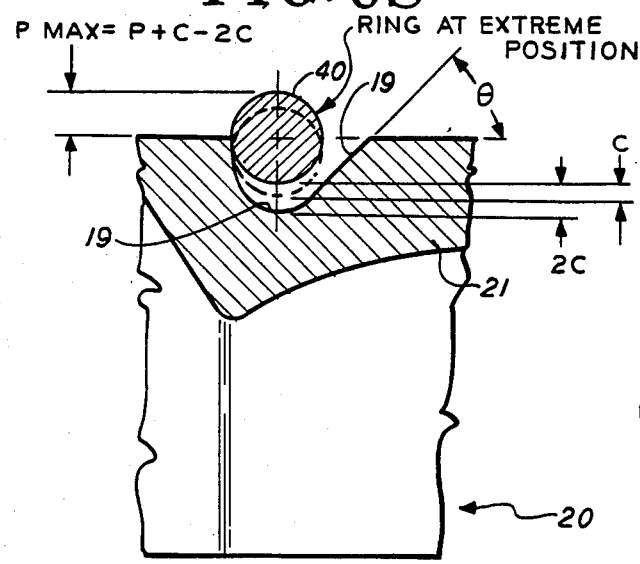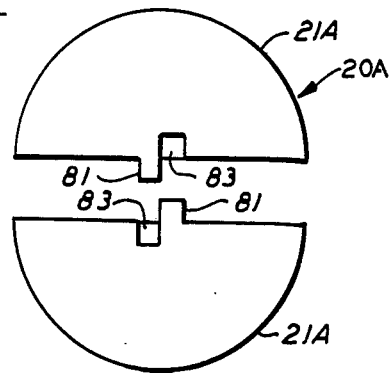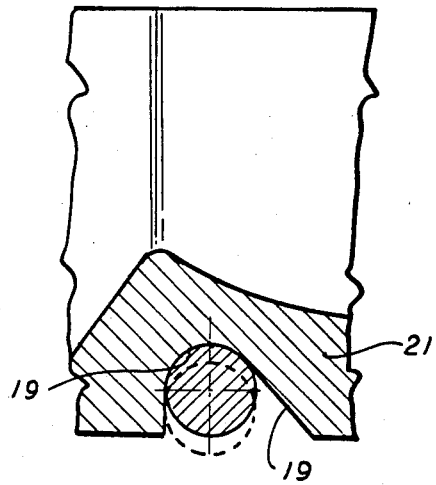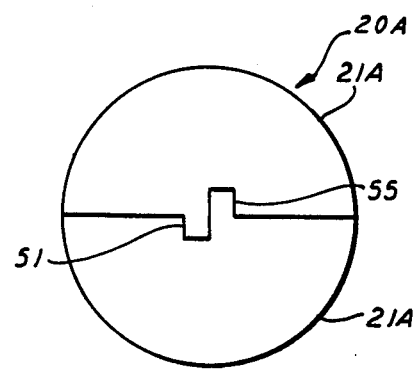

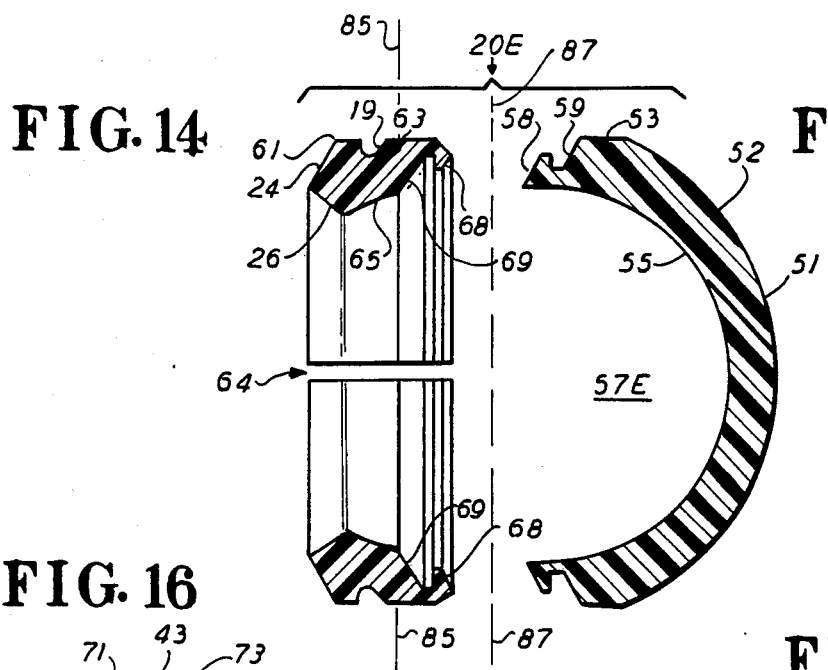
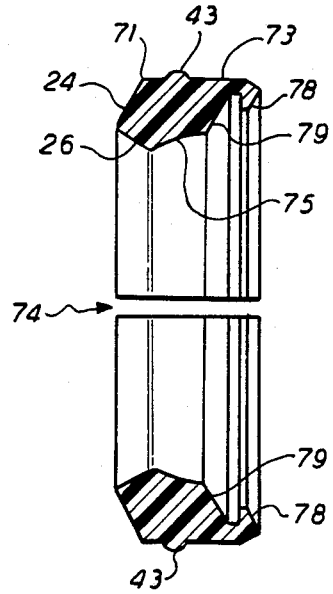
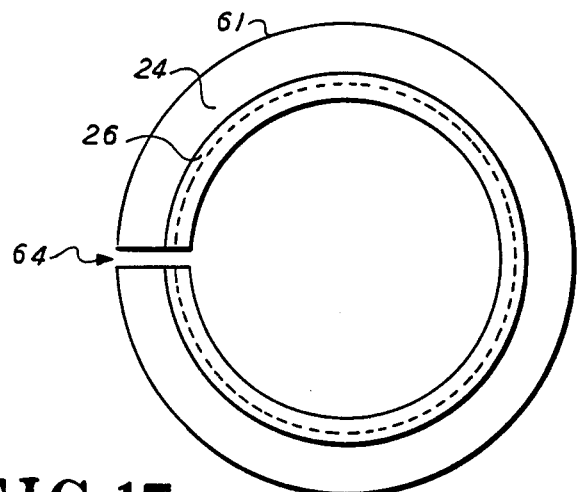
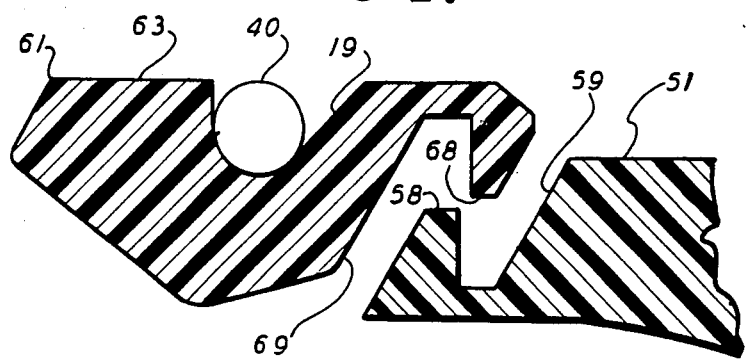

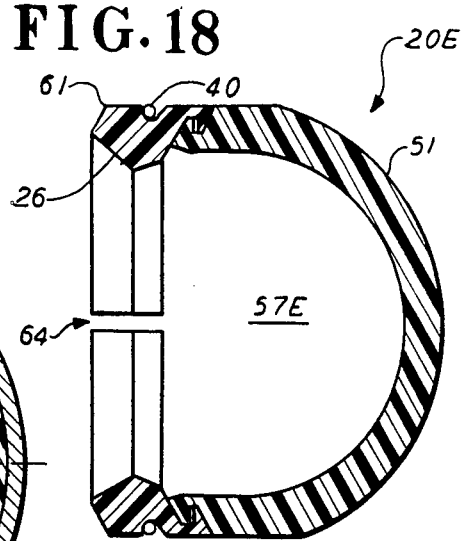
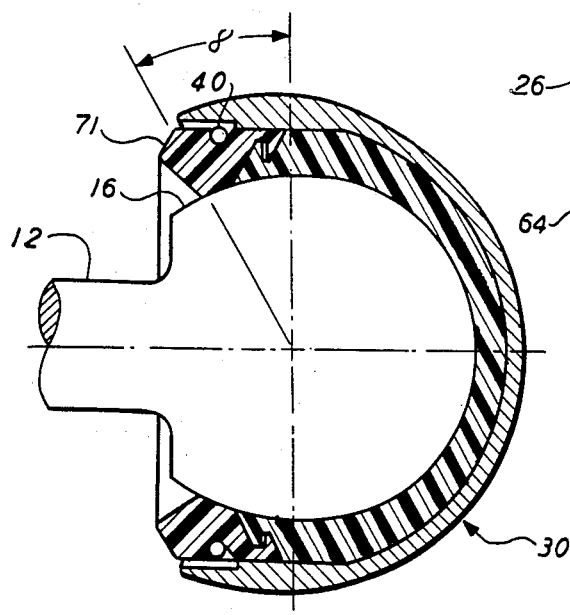
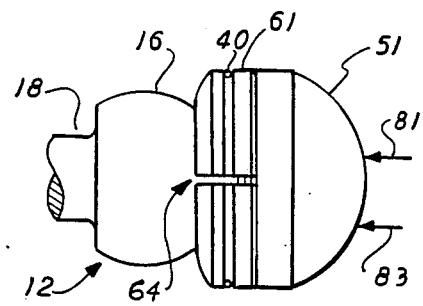
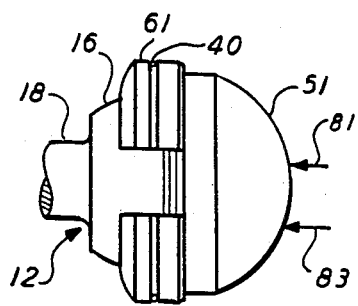
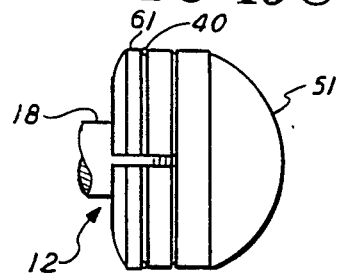
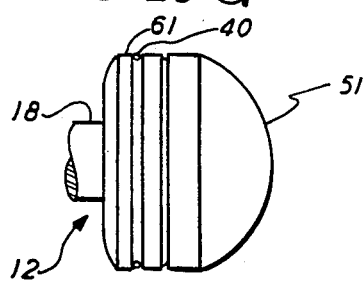

SPHERICAL KINEMATIC JOINT

CROSS-REFERENCE TO RELATED APPLICATIONS

This application is a division of application Ser. No. 351,760 filed Feb. 24, 1982, pending.

BACKGROUND OF THE INVENTION

This invention relates generally to an improved globular or spherical kinematic joint which, as known to those skilled in the art, provides, kinematically, three degrees of freedom of rotation; spherical kinematic joints are commonly used in machinery applications such as heavy machinery and business machinery and are also commonly used in various automotive applications such as tie rod connections. Such joints typically include a member providing a ball or spherical head, an intermediate bearing insert providing a cavity or seat for receiving the spherical head and a third member providing another cavity or seat for receiving the bearing insert with the ball or spherical head residing therein. Many applications require that such joint be capable of resisting dislocation when it is at its extreme limits of rotational movement and that it resist separation under a load tending to pull the connected joint members apart. The structure of such joints is well known to those skilled in the art and it is also well known that such joints may be comprised of many different structural elements.

As is further known, it is often desired that such joints eliminate or minimize axial play or slop between the connected joint members. Joints illustrating this may be seen in U.S. Pat. Nos. 1,891,804 and 1,894,309 to W. A. Flumerfelt issued Dec. 20, 1932 and Jan. 17, 1933, respectively; U.S. Pat. No. 1,985,728 to G. B. Ingersoll issued Dec. 25, 1934; U.S. Pat. No. 3,220,755 to Gottschald et al. issued Nov. 30, 1965; and U.S. Pat. No. 3,401,965, to W. C. Wehner issued Sept. 17, 1968. All of the joints disclosed in these patents have provision for minimizing or eliminating axial play. These patents further illustrate two different types of spherical kinematic joint structure or construction. In the Flumerfelt and Ingersoll patents, the bearing inserts comprise separate bearing insert segments which are assembled over the ball or spherical head and are then inserted into a housing where they are retained by various means. The Wehner patent shows a different type of joint structure or construction which includes a load carrying bearing insert and a retaining collar for preventing dislocation and tensile separation of the connected joint members. The Gottschald et al. patent illustrates a unitary construction wherein the bearing insert contains multiple splits of the front face near the opening providing a multiplicity of fingers or arcuate sections which expand outwardly upon being forced into engagement with the ball or spherical head; after such assembly, the bearing insert and ball are then inserted into the cavity or seat of the third member whereby the third member prevents outward expansion of the fingers thereby trapping the bearing insert on the ball. Additional or secondary means are then provided to hold the bearing insert in the cavity of the third member thereby providing a joint that resists tensile separation and dislocation.

Recently, spherical kinematic joints have found application in human joint prostheses. In prosthetic applications, ease of assembly and disassembly of the joint elements or members are of great importance. The use of an intermediate bearing insert comprised of a plurality of bearing segments unconnected when not assembled in the joint is undesirable in prosthetic applications since handling and holding of the bearing segments against the head while assembling the head and bearing segments with the third member can be awkward, particularly to an operating surgeon working inside of a surgical cavity. Although a bearing insert having flexible fingers or arcuate sections reduces the amount of assembly force that would be required were the fingers not present, such flexible fingers can still be quite awkward to the operating surgeon since to provide the required or desired dislocation and separation resistance and strength the fingers must be quite stiff which, in turn, requires that considerable assembly force still be applied by the operating surgeon.

As is well known to those skilled in the art, in prosthetic joint applications, low assembly force and ease of assembly are of great importance because of the need to minimize assembly time and because of the difficulties under which the surgeon must operate. Often, the field of view is obscured and joint elements or members are slippery because of coating with blood and fat which can result in dropping of the joint elements thereby causing a further problem since such joints must be sterile and upon dropping they must be resterilized, or replaced, while the surgical cavity remains open. Further, on occasion, because of surgical emergency or other intra-operative difficulties, it is desirable to be able to disassemble the joint members, preferably in a manner which avoids the same difficulties of assembly noted above, i.e., excessive disassembly forces and multiple unconnected bearing insert members which are difficult to handle. Thus, joints which are satisfactory for machinery applications where fixtures and other tooling may be conveniently used to assemble joint members need improvement for their effective utilization in prosthetic joints.

Patents disclosing prosthetic joints include U.S. Pat. No. 3,813,699 to Richard P. Giliberty, issued June 4, 1974; U.S. Pat. No. 3,863,273 to Robert G. Averill, issued Feb. 4, 1975; U.S. Pat. No. 4,044,403 to D'Errico issued Aug. 30, 1977; and U.S. Pat. No. 4,241,463 to Alex Khovaylo issued Dec. 30, 1980. The prosthetic joint disclosed in the Giliberty patent provides a prosthetic joint which is resistant to dislocation and separation and partially avoids the assembly problems noted above by providing a unitary structure including both the bearing insert and the acetabular cup thereby minimizing the handling of various joint members during the assembly and disassembly process. However, the unitary structure of the bearing insert and the acetabular cup does not allow for ease of assembly and disassembly with high separation resistance, since the opening into the spherical cavity of the bearing insert which receives the ball-shaped femoral head is incapable of substantial outward expansion or flexing upon being forced into engagement with the ball-shaped head and therefore the Giliberty prosthetic joint requires either extremely high assembly or disassembly forces and/or relatively low resistance to dislocation and separation forces. The prosthetic joint disclosed in the Averill patent partially overcomes the problem of excessively high assembly or disassembly forces by utilizing, as in the Gottschald et al. patent, an intermediate bearing insert provided with a plurality of arcuate sections at the entry into the spherical seat for receiving the ball which arcuate sections upon being forced into engagement with the femoral head still require a generally undesirably high manual force to expand outwardly to permit entry of the ball-shaped head into the spherical seat of the intermediate bearing insert. The Averill prosthetic joint also utilizes a tab provided on the bearing insert to prevent separation of the bearing insert from the acetabular cup; however, such structure introduces undesirable axial play into the prosthetic joint. Similarly, the prosthetic joint disclosed in the D'Erricho patent is also a partial solution to the above-noted assembly problem in that the assembly forces required to assemble the joint members are reduced below those required to assemble the joint members of the Giliberty prosthesis given a predetermined dislocation and separation resistance; this is accomplished by the use of flexible lips provided on the bearing insert acting against the spherical head or ball of the first member and/or the cavity in the third member or acetabular cup. Such joint construction, however, is not readily disassemblable without some damage to the bearing insert and does not provide the desirable combination of low force of manual assembly and high separation resistance needed by an operating surgeon intra-operatively. The Khovaylo prosthetic joint provides structure which allows for low assembly force of the bearing insert onto the head but employs a solution similar to that disclosed in the D'Erricho patent for assembly of the third member or acetabular cup onto the bearing insert. Further, the internal retaining ring of the Khovaylo prosthetic joint operates in a manner which produces end play between the spherical ball and the bearing insert. Further, the Khovaylo prosthetic joint does not provide for convenient assembly or disassembly of the bearing insert from the third member or acetabular cup intra-operatively. As is further known to those skilled in the prosthetic joint art, physically separate acetabular cups and bearing inserts are desirable in prosthetic joint applications in order to minimize the cost of stocking various sized prostheses and in order to minimize sterilization costs associated with such joints.

As is still further known to those skilled in the art, the bearing inserts of the above-noted patents, provide an overlap which, upon the ball-shaped head being received within the bearing insert and the bearing insert with the ball-shaped head seated therein being received within the insert housing, prevents dislocation of the ball-shaped head from the bearing insert during rotational movement between the ball-shaped head and the insert housing cup.

SUMMARY OF THE INVENTION

The improved spherical kinematic joint of the present invention overcomes the above-noted prior art problems by providing various bearing insert embodiments which allow ease and convenience of assembly and disassembly, particularly assembly, by providing a plurality of substantially physically distinct bearing inserts in a sub-assembly such that the bearing inserts are effectively a unitary structure for the purpose of assembly and disassembly but which bearing segments expand easily with low manual force during assembly and disassembly of the various bearing insert embodiments from the head and/or cavity or spherical seat in the third member, such as for example in the prosthetic joint embodiments, an acetabular cup. Further, such ease of assembly and disassembly can be accomplished while retaining great dislocation and separation resistance and in some embodiments is accomplished in a manner which does not introduce significant axial play.

DESCRIPTION OF THE DRAWINGS

FIG. 2 is a cross-sectional view of a first embodiment of a split bearing insert of the present invention;

FIG. 2(a) is a partial front view of a portion of the split bearing insert shown in FIG. 2;

FIG. 3 is a cross-sectional view of an acetabular cup of the present invention, particularly useful when the improved spherical kinematic joint of the present invention is embodied as a prosthetic hip joint;

FIG. 3(a) is a partial front view of a portion of the acetabular cup;

FIGS. 4(a) and (b) are, respectively, cross-sectional views of alternate embodiments of retaining rings;

FIGS. 5(a)-(c) are, respectively, side, top and an enlarged view of a release ring useful for disassembling the elements of the improved spherical kinematic joint of the present invention;

FIGS. 7(a)-(c) are views illustrating the utility of scallops which may be provided on the various split bearing inserts of the present invention to reduce the amount of radial expansion required for assembly of the bearing inserts to the femoral head of a femoral stem upon the improved spherical kinematic joint of the present invention being embodied as a prosthetic joint;

FIGS. 8(a) and (b) are cross-sectional, diagrammatic illustrations showing the advantage of providing greater engagement between a retaining ring and the external grooves provided on a bearing insert than between the retaining ring and the internal circumferential groove provided on an acetabular cup, upon the present invention being embodied as a prosthetic hip joint and utilizing a retaining ring; and FIGS. 9(a)-(c), FIG. 10, FIG. 11, FIGS. 12(a)-(d), and FIGS. 13-20 are, respectively, alternate embodiments of various split bearing inserts of the improved spherical joint of the present invention, particularly when embodied as a prosthetic hip joint.

DESCRIPTION OF THE PREFERRED EMBODIMENTS

Figures 1, 4:
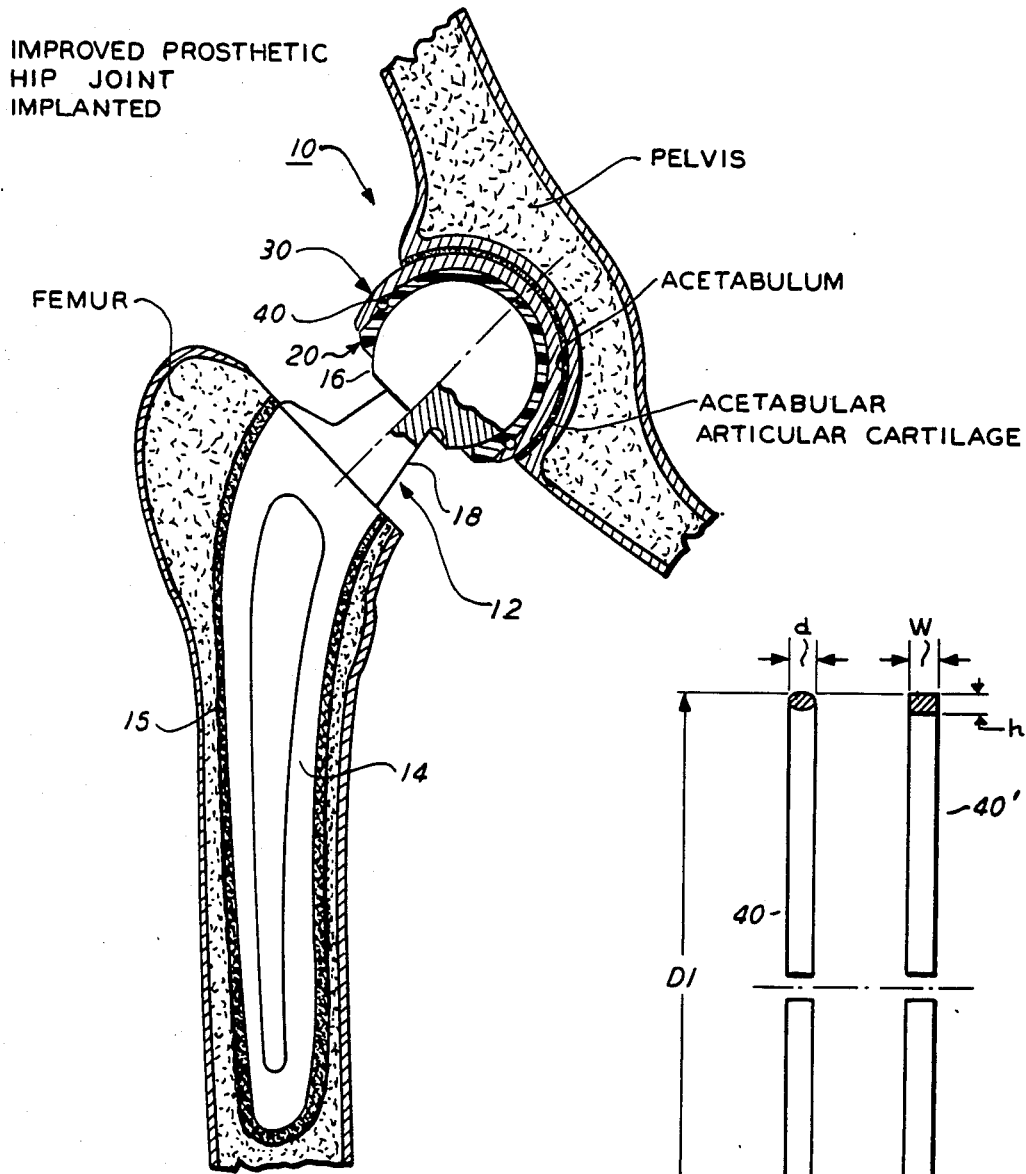
FIG. 1 is a diagrammatic illustration, in cross-section, showing the improved spherical kinematic joint of the present invention, embodied as a prosthetic hip joint, implanted in a pelvis and femur.

Referring now to FIG. 1, there is shown a first embodiment of the improved spherical kinematic joint of the present invention embodied as a prosthetic hip joint 10 which is shown implanted. The prosthetic hip joint 10 includes the following components: a femoral component 12, sometimes referred to in the art as an intermedullary stem or femoral insert; a split bearing insert 20; an acetabular cup 30; and a retaining ring 40.

The femoral component 12 includes a stem 14 which fixtures the component into the medullary cavity of the proximal femur, preferably but not exclusively with the aid of a grouting agent 15; a ball-shaped or spherical femoral head 16; and a neck region 18 which transfers load from the spherical femoral head 16 to the stem 14.

The split bearing insert 20, as may be better seen in FIGS. 2 and 2(a), includes a plurality, a pair being shown, of opposed identical split bearing segments or clam shell-shaped members 21—21; in this embodiment, each split bearing segment 21 is physically distinct from the other. Each segment 21 is provided with an outer spherical surface 22, an outer cylindrical surface 23 and an outer annular tapered surface 24; additionally, each segment 21 is provided with an inner spherical surface 25 and a chamfer or inner annular tapered surface 26. Further, in the embodiment shown, each segment 21 is provided with a generally U-shaped longitudinally extending surface 29 which will be of the same shape as the cross-hatched area of FIG. 2 but without the gap. Each outer spherical surface 22 merges with the inner end of an outer cylindrical surface 23 and the outer end of each cylindrical surface 23 terminates with the inner end of an outer annular tapered surface 24; similarly, each inner annular tapered surface 26; and the outer ends of the annular tapered surfaces 24–26 intersect or merge as shown, preferably with a slight radius r. When placed in opposed relationship as shown in FIG. 2, the inner spherical surfaces 25-25 of the clam shell-shaped members 21-21 cooperatively provide a spherical cavity or seat 27 for receiving the spherical femoral head 16 (FIG. 1) of the femoral component 12 (FIG. 1) and thus it will be understood that the spherical cavity or seat 27 preferably closely matches the shape of the spherical femoral head 16 with the diameter of the femoral head 16 being larger than the opening to the seat 27 provided by the chamfer 26. A pair of scallops or beveled surfaces 28-28 may be provided on each member 21 contiguous with and merging into the longitudinally extending surfaces 29, beveled surfaces 28-28 facilitate the insertion of the spherical femoral head 16 of the femoral component 12 into the spherical cavity 27 by reducing the amount of expansion of the split bearing insert 20 required for insertion. Lastly, an external circumferential groove 19 is provided in each outer cylindrical surface 23 for receiving or at least partially receiving, the flexible retaining ring 40 shown in FIG. 4(a). The depth and width of the groove 19 are sufficient to permit the retaining ring 40 to be received completely within the groove upon the ring being compressed radially inwardly. It will be understood that, prior to the assembly of the spherical prosthetic hip joint components for implantation, the first function of the retaining ring 40, upon being received, or at least partially received, within the external circumferential grooves 19, is that of maintaining the clam shell-shaped members 21-21 together in a sub-assembly and in generally opposed relationship as illustrated in FIG. 2 with the generally U-shaped longitudinally extending surfaces 29 engaged in a plane of contact or separation extending through the center line C/L.

The acetabular cup 30, as may be best seen in FIG. 3, is provided with a smooth outer spherical surface 31 which terminates at the inner end of an outer annular tapered surface 32, the cup is further provided with an inner spherical surface 33 which merges at its outer end with the inner end of a cylindrical inner surface 34 which at its outer end merges with the inner end of a chamfer or inner annular tapered surface 35; the tapered surfaces 32–35 intersect or merge at their outer ends as shown. An internal circumferential groove 37 is provided near the outer end of inner cylindrical surface 34 for receiving the retaining ring shown in FIG. 4(a). The outer spherical surface 31 preferably closely matches the acetabular cartilage or natural acetabulum (FIG. 1), the acetabular articular cartilage not always being present depending upon the degeneracy of the joint, and the inner spherical surface 33 and inner cylindrical surface 34 cooperatively provide a cavity or seat 38 for receiving the split bearing insert 20. Preferably, the inner cylindrical surface 33 and inner cylindrical surface 34 of the acetabular cup 30 closely match the outer spherical surfaces 22-22 and the outer cylindrical surfaces 23-23, respectively, of the split bearing insert 20. As is further shown in FIGS. 3 and 3(a), the acetabular cup 30 is provided with a plurality of radially disposed slots or grooves 39 extending axially into the inner annular tapered surface 35 and the outer portion of the inner cylindrical surface 34; upon the retaining ring 40 being received within the circumferential grooves 19 and 37 and upon the spherical femoral head 16, split bearing insert 20 and acetabular cup 30 being assembled as illustrated in FIG. 1, the radially disposed grooves 39 are for providing external access to the retaining ring 40 by the radially disposed prongs 44 of the release tool 46 shown in FIGS. 5(a) and 5(c) for disassembly of the split bearing insert 20 and the spherical head 16 of the femoral component from the acetabular cup 30, as will be explained in detail below.

Figure 6A:
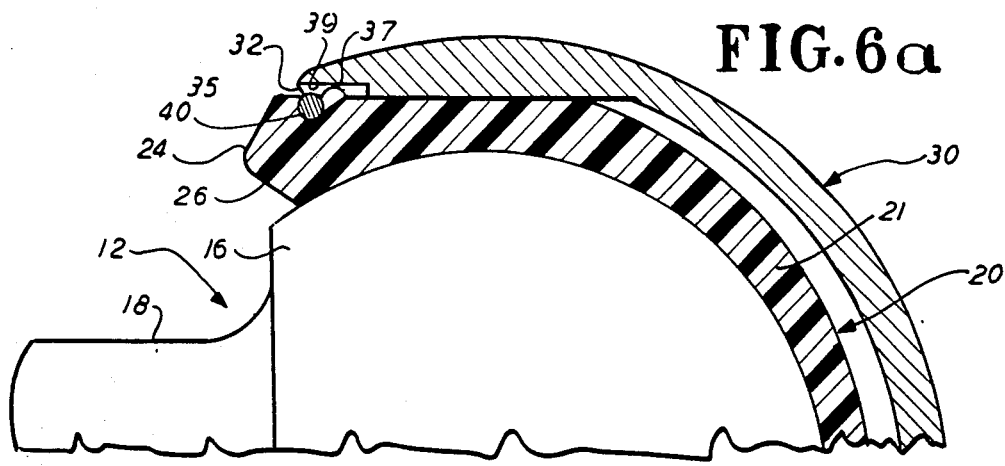
FIGS. 6(a) and (b) are, respectively, sequential views, in cross-section, illustrating assembly of one embodiment of the present invention.
Figure 6B:
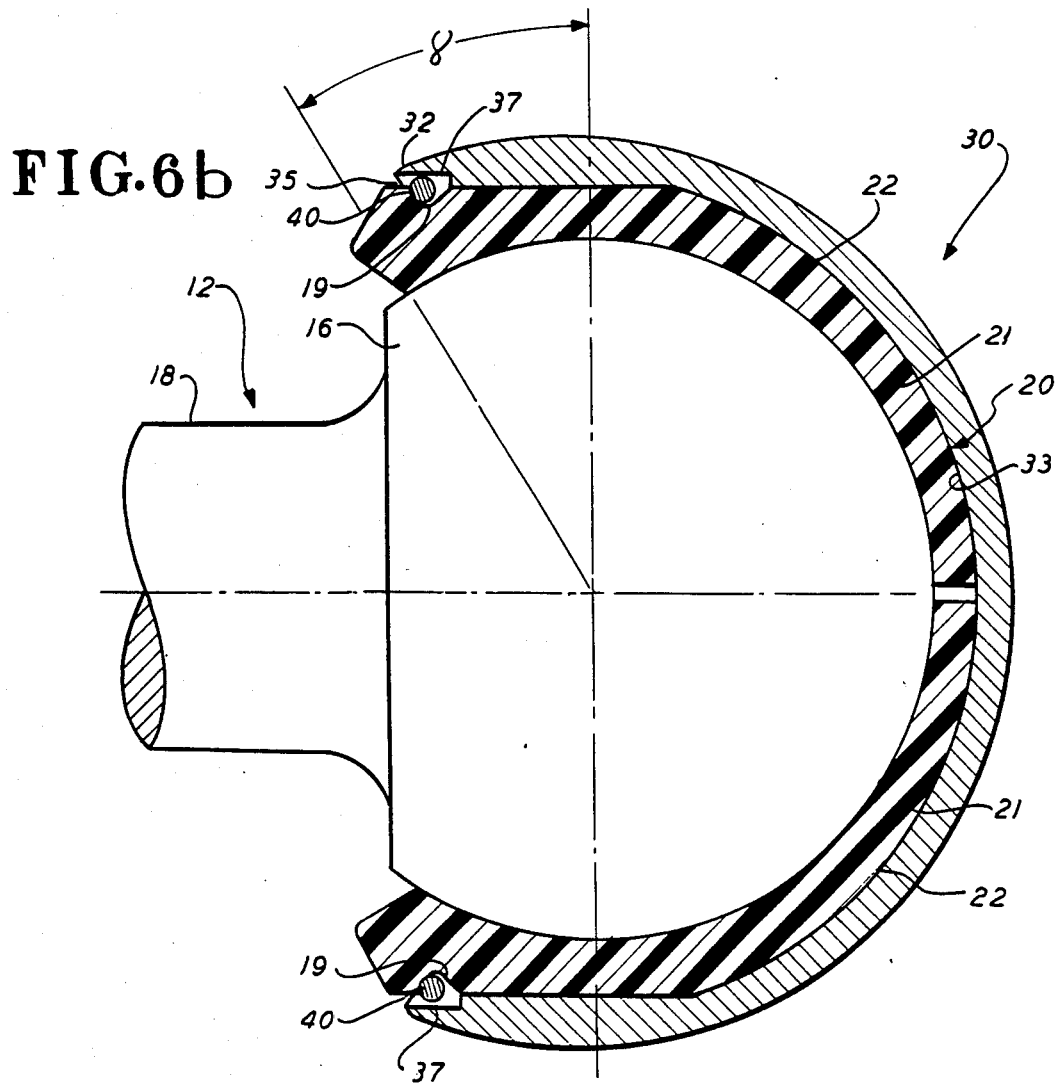

The spherical prosthetic hip joint 10, embodying the present improved spherical joint invention, is implanted as follows: the femoral component 12 is implanted in the femur as described above and as illustrated in FIG. 1, the forward portion or chamfer 26 of the split bearing insert 20, with the retaining ring 40 residing, or at least partially residing, within the external circumferential grooves 19 and maintaining the split bearing segments 21-21 together in a sub-assembly as described above, is forced (manual force supplied by the operating surgeon being more than sufficient) into engagement with the spherical femoral head 16 which is larger in diameter than the opening to the seat 27 whereupon the split bearing segments 21-21 expand radially by generally pivoting outwardly (i.e. pivoting generally radially outwardly) about their rearward portions (such expansion being facilitated by the scallops 28 if provided) to allow the femoral head to be received within the split bearing insert 20 and to be seated within the spherical cavity or seat 27, then the acetabular cup 30 is then pushed over the split bearing insert 20 to cause the chamfer or inner annular tapered surface 35, as illustrated in FIG. 6(a), to engage the retaining ring 40 and compress it radially inwardly completely within the external circumferential grooves 19 provided on segments 21-21 thereby allowing the acetabular cup to pass over the retaining ring 40 until as illustrated in FIG. 6(b), the inner spherical surface 33 of the acetabular cup meets or engages the outer spherical surfaces 22-22 of the low-friction split bearing insert 20. At this point, the external circumferential grooves 19-19 provided in the segments 21-21 are aligned axially with the internal circumferential groove 37 provided in the acetabular cup 30 whereupon the retaining ring 40 expands radially outwardly to be partially received within the internal circumferential groove 37 and partially within the external circumferential grooves 19-19. The retaining ring 40 now performs its second function; it retains the acetabular cup on and over the split bearing insert 20 with the spherical femoral head 16 received therein thereby preventing separation (e.g. axial dislocation) between the bearing insert (with the femoral head seated therein) and the acetabular cup during joint rotation. All three components of the spherical prosthetic hip joint 10 are now assembled and the acetabular cup 30 is inserted within the acetabulam as illustrated in FIG. 6(b).

The manner in which such scallops or beveled surfaces 28-28 facilitate the insertion of the spherical femoral head 16 into the spherical cavity 27 by reducing the amount of radially outward expansion required by the split bearing insert or segments 21-21 is illustrated diagrammatically in greater detail in FIGS. 7(a)-(c). As illustrated in FIG. 7(b), upon the split bearing segment 21' not being provided with the scallops or beveled surfaces 28-28, the segment must be expanded radially outwardly a distance L1 to permit insertion of the spherical head 16 into the spherical cavity or seat 27, whereas, upon the split bearing segment 21 being provided with the scallops or beveled surfaces 28-28 as illustrated in FIG. 7(c), the segment 21 must be expanded radially outwardly a lesser distance L2 to permit such spherical femoral head insertion wherein, it will be understood as illustrated, the distance L2 is less than the distance L1 by substantially the height S of the scallops 28-28.

In the embodiment of the present invention illustrated in FIG. 6(b), the overlap angle γ is approximately 30° and the rotational or pivotal motion provided is approximately 60°.

For disassembly, the release tool 46, FIGS. 5(a) and (b) may then be inserted over the neck region 18 of the femoral component 12, FIG. 6(b), entry being permitted by the gap or opening 48 provided in the release tool, FIG. 5(b), and the radially disposed prongs 44 are inserted into the radial grooves 39 (FIG. 3) provided in the acetabular cup 30 to cause the chamfered edges 47 of the release tool, FIG. 5(c), to pass over the retaining ring 40 and depress the ring completely within the external circumferential grooves 19-19 provided on the split bearing segments 21-21 allowing the withdrawal of the acetabular cup 30 from over the split bearing insert 20 thereby disassembling the acetabular cup from the split bearing insert 20 and the spherical femoral head 16 received within the spherical cavity 27 or the insert 20. For further disassembly of the split bearing insert 20 from the spherical femoral head 16, force, readily supplied manually by the operating surgeon, is applied to the split bearing insert 20 to pull it away from the spherical femoral head 16 whereupon the split bearing insert segments 21-21 move radially outwardly and the split bearing insert 20 is readily withdrawn, facilitated by the scallops 28 if provided, from over the spherical femoral head 16 leaving the femoral component 12 implanted in the femur if desired. It will be noted that by providing the release tool 46 (FIGS. 5(a) and 5(b)) with the gap or opening 48, a one piece release tool is provided which may be utilized to disassemble the acetabular cup from the split bearing insert 20 and spherical femoral head 16 received within the cavity or seat 27, without requiring removal of the femoral component 12 from the femur (FIG. 1).

It will be further understood by those skilled in the art that the wearing properties of the split bearing insert 20 may be improved by dimensioning the split bearing segments 21-21 on the dimension of the spherical femoral head 16 such that upon assembly of the bearing insert 20 to the spherical femoral head 16, a gap or space is provided between the generally U-shaped longitudinally extending surfaces 29 (FIG. 2) to permit a lubricant, which in the case of a spherical prosthetic hip joint is synovial fluid, to reach to the bearing surfaces of the spherical joint and aid in removal of wear debris from the bearing surfaces by providing convenient passages to the surrounding regions.

It will be further understood, that while in the preferred embodiments of the present invention the retaining ring 40 is of circular transverse cross-section, particularly because of greater availability and lower cost of such circular cross-sections, as illustrated in FIG. 4(b), other retaining ring cross-sections may be utilized, such as square, rectangular, etc. may be utilized and, of course, the shapes of the external circumferential grooves 19-19 on the segments 21-21 and the internal circumferential groove 37 provided on the acetabular cup 30 will be of suitable cross-sectional shape. It will be noted that the retaining ring and grooves need not be of complementary shape; it has been found that a ring of circular cross-section will function properly in a groove of generally rectangular cross-sectional shape with side walls generally perpendicular, and a bottom generally parallel, to the outside cylindrical surface. Further, it will be understood and as illustrated in FIG. 4, the retaining ring 40' (FIG. 4(b)), is provided in transverse cross-section with a width "w" and a height "h" whereas, since the transverse cross-sectional shape of the retaining ring 40, FIG. 4(a), is circular, both the width and height of the retaining ring 40, in transverse cross-section, are equal to the diameter "d."

It has been found to be desirable to provide greater engagement "e" as shown in FIG. 8(a), between the retaining ring 40 and the external circumferential grooves 19-19 provided in the bearing insert 20 than between the retaining ring 40 and the internal circumferential groove 37 provided in the acetabular cup 30 in order to produce less possible protrusion of the retaining ring 40, out of groove 19 during assembly. This protrusion may be understood by reference to FIGS. 8(a) and 8(b). The smaller protrusion out of external circumferential groove 19 of the bearing insert 20 allows the use of a smaller chamfer or inner tapered annular surface 35 at the entrance into the spherical cavity or seat 38 of the acetabular cup. This smaller chamfer or inner annular tapered surface 35 produces less interruption in the face or entrance portion of the acetabular cup 30 thus producing a better appearance and allows the use of a thinner cup wall "t," FIG. 3, thereby allowing an increased range of acetabular cup sizes that will fit over a given bearing insert, e.g. bearing insert 20 of FIG. 2.

Referring again to FIG. 8, it may be seen that the maximum protrusion $P_{max}$ occurs when one side of the ring is pushed or falls fully into external groove 19 causing the other side of the ring to protrude to the maximum extent. It will be understood that the smallest maximum protrusion "$P_{max}$," for a given engagement "e" between the ring and groove is obtained when the depth of the internal groove 37 is equal to the cross-sectional diameter "d" of retaining ring 40. For this case, the maximum protrusion is:

$$P_{max} = P + C \quad (1)$$

where P is the protrusion of the retaining ring 40 when its axis coincides with the axis of the bearing insert and C is the clearance between the ring and the bottom of the external groove 19 with the retaining ring is so aligned. Now $$d = P + e$$

or $$P = d - e \tag{2}$$

and $$C = d - e \tag{3}$$

Now, if the ring is placed so that one side is fully within groove 19 as shown in FIG. 8(b), then the protrusion $P_{max}$ is $$P_{max} = 2(d - e) \tag{4}$$

Thus, it may be seen that increasing "e" reduces $P_{max}$.

With circular cross-sections in order to provide greater engagement between the external bearing insert groove 19 and the retaining ring 40 than between acetabular internal groove 37 and the retaining ring 40, it is necessary to taper the posterior face 37 of insert groove 19 to prevent retraction of the ring. To prevent such retraction, the angle as shown in FIG. 2 may be computed from:

$$\theta \leq \cos^{-1}(2e/d - 1) \tag{5}$$

where "e" is engagement between the retaining ring 40 and the insert groove 11 and "d" is a cross-sectional diameter of the retaining ring 40. The outer diameter D1 of the retaining ring 40 is made essentially equal to the diameter D2 of the acetabular cup internal groove 37 as shown in FIGS. 4 and 3, respectively.

Alternate embodiments of the improved spherical kinematic joint of the present invention, also embodied as improved spherical prosthetic hip joints, are provided and are illustrated in FIGS. 9(a)-(c), 10, 11 and 12(a)-(d). These embodiments include various alternate bearing inserts having various hinge or pivot type connections between the split bearing segments at their rearward portions which reduce or eliminate the possibility of the segments disengaging from each other and from the retaining ring during assembly and disassembly of the components of the improved spherical joint. It will be further understood that these alternate embodiments include the femoral component 12, acetabular cup 30, and in some embodiments, the retaining ring 40 of FIG. 1; the alternate bearing inserts are given numerical-alpha designations, e.g. 20A, 20B, etc. to distinguish them from the bearing insert 20 of the first embodiment and where the structure and surfaces of these alternate bearing insert embodiments are identical to those of the first embodiment, they are given the corresponding numerical designations but where different, they are given a numerical-alpha designation corresponding to the alpha designation of the bearing insert alternate embodiment.

The first alternate embodiment, FIGS. 9(a), 9(b) and 9(c), includes the split bearing insert 20A which includes a plurality, a pair being shown, of opposed identical split bearing segments 21A-21A each of which is provided at its rearward portion with an outwardly extending tab 81 and an inwardly extending recess 83. Upon assembly, as illustrated generally in FIGS. 9(b) and 9(c), the tabs 81 are received in the recesses 83 to cooperatively provide a pivot or hinge-type connection, about which the segments 21A-21A pivot outwardly to permit insertion of the spherical femoral head 16 into the spherical cavity or seat 27A provided by the inner spherical surfaces 25A-25A of the segments 21A-21A.

Figure 10:
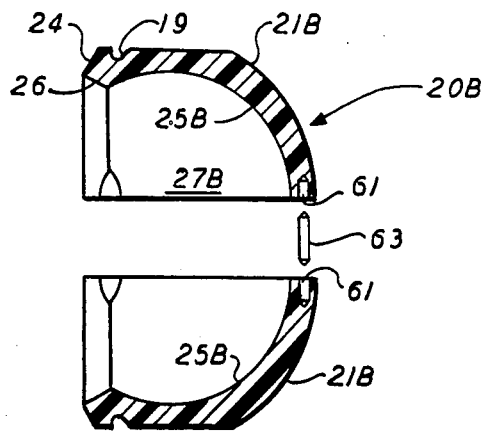

A second alternate embodiment is illustrated in FIG. 10 and includes the alternate split bearing insert 20B comprised of the plurality of opposed identical split bearing segments 21B-21B each of which members, as illustrated, is provided at its rearward portion with an inwardly extending hole 61 for receiving one end of a flexible pin 63; otherwise, this further alternate embodiment further includes the spherical joint components described hereinabove. Upon insertion of the flexible pin 63 into the opposed and axially aligned holes 61-61, the split bearing segments 21B-21B pivot outwardly about the hinge type connection provided cooperatively by the holes 61-61 and the flexible pin 63 to expand to the split bearing insert 20B radially outwardly to permit the spherical femoral head 16 to be received within the internal seat or cavity 27B provided internally of the split bearing insert 20B by the inner spherical surfaces 25B-25B.

Figure 11:
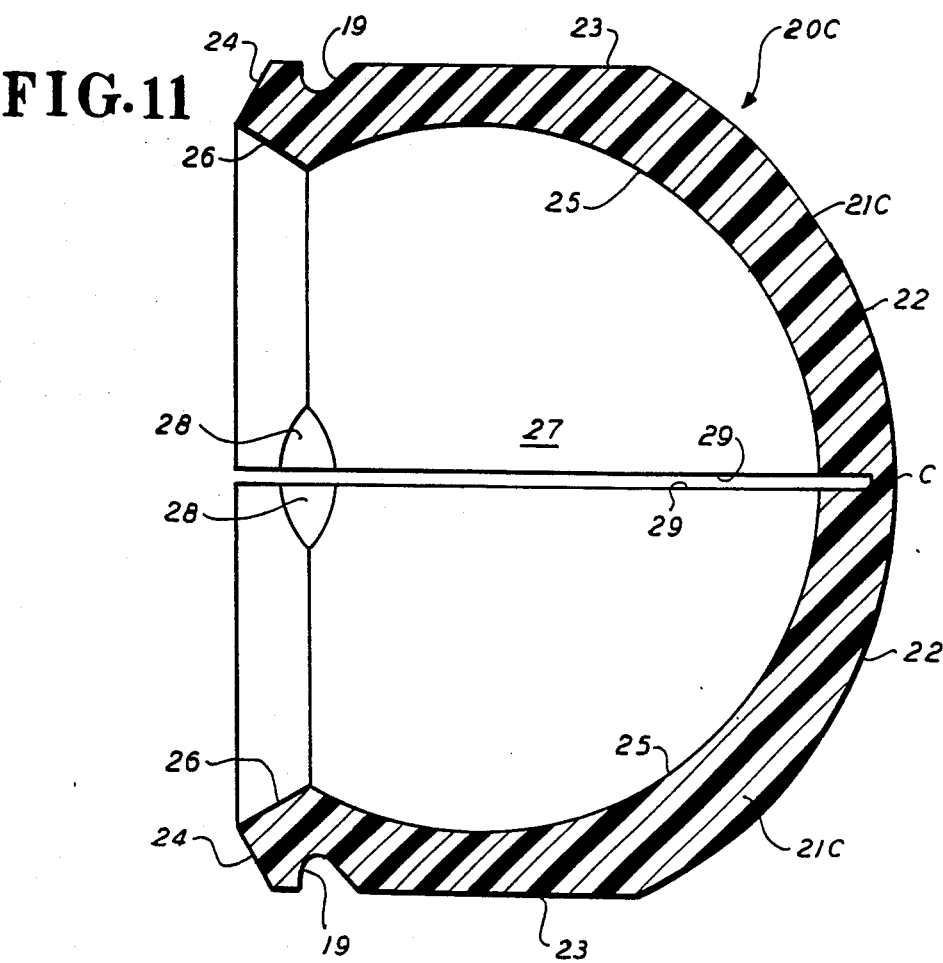

Referring to a third alternate embodiment illustrated in FIG. 11, it will be understood that the split bearing insert 20C is substantially identical to the split bearing insert 20 illustrated in FIG. 2 but wherein the split bearing segments 21-21 of FIG. 2 are physically distinct from each other, the split segments 21C-21C of the embodiment of FIG. 11 are connected or hinged together at their rearward portions by a relatively thin integral member C. The alternate embodiment including the low-friction split bearing insert 20C of FIG. 11 is assembled and disassembled in substantially the identical manner as the embodiment including the split bearing insert 20 of FIG. 2 except that upon radially outward expansion of the split bearing insert 20C of FIG. 11 to permit insertion of the spherical femoral head 16 into the spherical cavity or seat 27, the split bearing segments 21C-21C hinge or pivot radially outwardly about the thin, flexible integral member C.

Figure 12A:
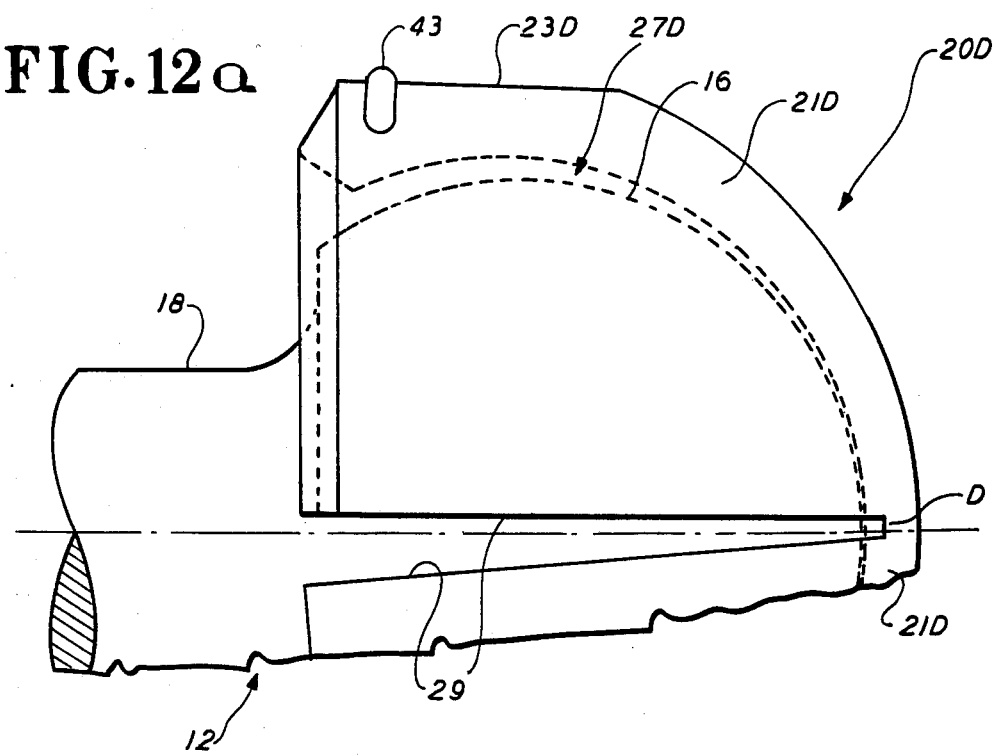
Figure 12B:
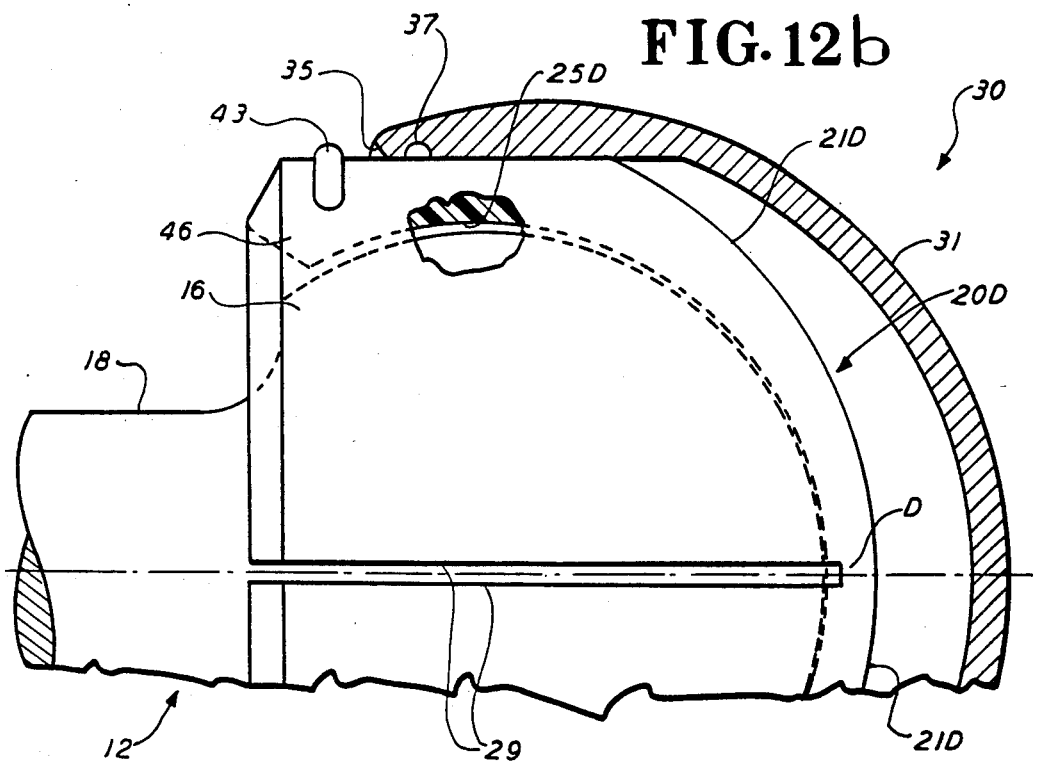
Figure 12C:
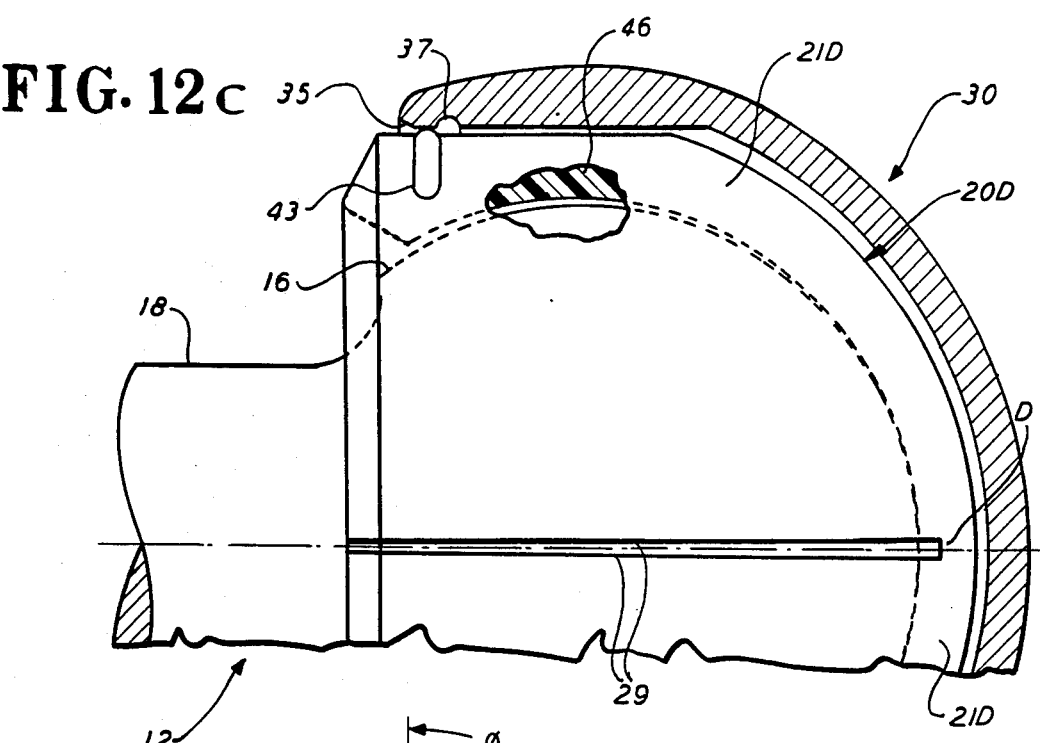
Figure 12D:
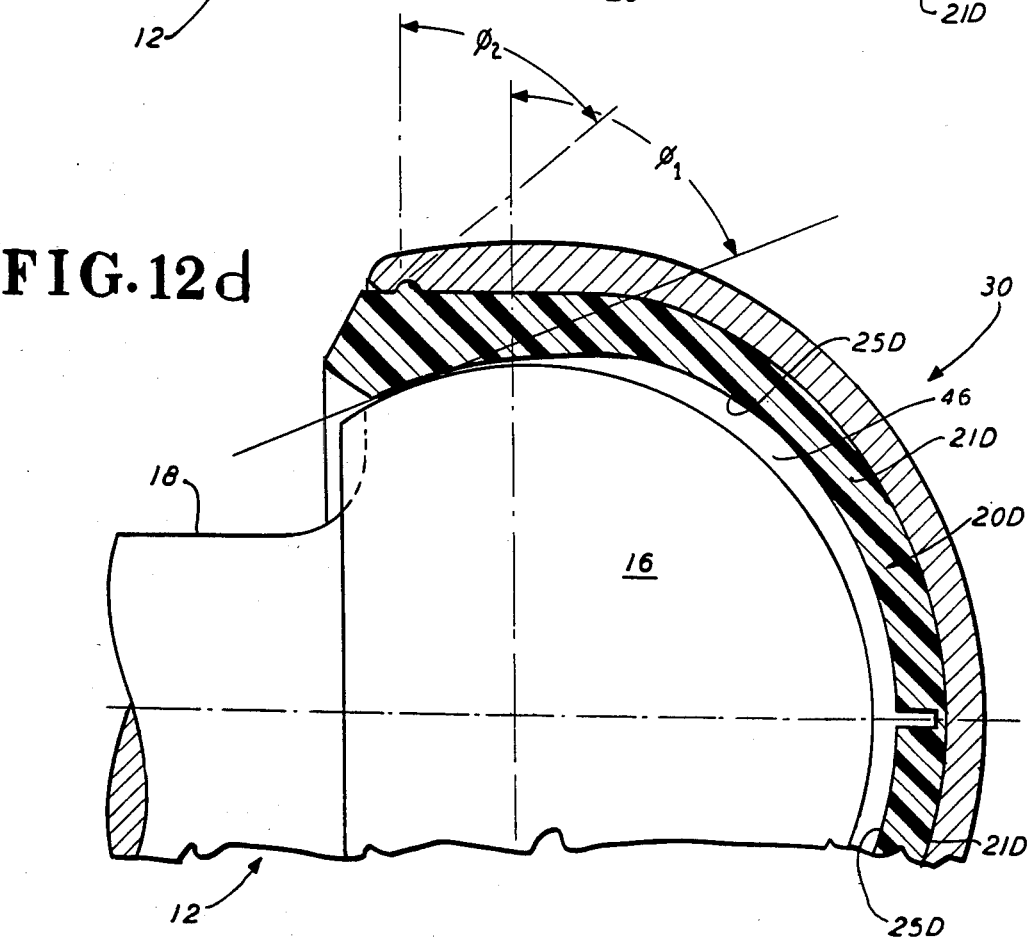

An alternate embodiment of the low-friction split bearing insert 20C illustrated in FIG. 11 is illustrated in FIGS. 12(a)-(d); this alternate split bearing insert is identified with numerical designation 20D. In this embodiment, the hinge or flexible member D is made sufficiently thick such that plastic deformation occurs when the split bearing segments 21D-21D are pivoted radially outwardly, as shown in FIG. 12(a) to permit insertion of the spherical femoral head 16 of the femoral component 12 into the split bearing insert 20D. Further, the inner spherical cavity or seat 27D provided in the interior of the split bearing insert 20D is made sufficiently large such that it is slightly larger than the spherical head 16 of the spherical component 12 thereby providing some clearance (indicated by numerical designation 46) between the spherical cavity 27B and the spherical femoral head 16 when the acetabular cup 30 is partially assembled onto the plastic bearing insert 20D as illustrated in FIG. 12(b). A partial outer circumferential ridge 43 is formed integrally on the outer cylindrical surface 23D of each split bearing segment 21D-21D which matches internal circumferential groove 37 provided on the acetabular cup when the cup and the split bearing insert 20D are fully assembled. Assembly of this embodiment is as follows. The femoral component 12 is implanted in the femur (FIG. 1) and the split bearing insert 20D and the spherical femoral head 16 are assembled as illustrated in FIG. 12(a) producing some deformation of the hinge or spherical flexible member D thereby producing some separation of the split bearing segments 21D-21D at their forward portions or inferior aspect as illustrated in FIG. 12(a). The acetabular cup 30 is then partially assembled onto the split bearing insert 20D as illustrated in FIG. 12(b) forcing the segments 21D-21D together against the resistance of the flexible member D. As assembly further progresses, the chamfer or inner tapered annular surfaces 35 engages the partial circumferential ridges 43 and presses forward portions or inferior aspect of the segments 21D-21D together as illustrated in FIG. 12(c). This action is allowed by the clearance 46 between the spherical femoral head 16 and the inner spherical surface 25D of the split bearing insert 20D and by the gap or spacing between the generally U-shaped longitudinally extending surfaces 29. Upon completion of assembly, the external, circumferential ridges 43 provided on the exterior of the split bearing insert 20D will be axially aligned with the internal groove 37 provided on the forward portion of the interior of acetabular cup 30 allowing the ridges 43 to engage the groove 37 by the spreading action of hinge segment or spherical bridge D. Disassembly or separation of the acetabular cup 30 from the split bearing insert 20D is prevented by the wedging action of the spherical femoral head 16 against the forward portion of the inner spherical surfaces 25D of the split bearing insert 20B and such separation will be prevented where the contact tangent $\phi 1$, as illustrated in FIG. 12(d) is greater than contact tangent $\phi 2$.

Disassembly is provided in the same manner described above by using the release tool 46 of FIG. 5.

A still further alternate embodiment of the improved spherical kinematic joint of the present invention, also embodied as an improved spherical prosthetic hip joint, is provided and is illustrated in FIGS. 13-20. This further alternate embodiment includes an alternate split bearing insert 20E which includes a plurality of physically distinct split bearing segments, namely the generally spherically-shaped primary bearing segment 51 of FIG. 13 and either the generally annularly shaped, radially or circumferentially split bearing segment or collar 61 of FIG. 14 provided with the external circumferential groove 19 or the generally annularly shaped, radially or circumferentially split bearing segment or collar 71 of FIG. 16 provided with the partial or complete external circumferential ridge 43.

As shown in FIG. 13, the primary bearing segment 51 is provided with an outer spherical surface 52, an outer cylindrical surface 53 and an inner spherical surface 55; additionally, the primary bearing segment 51 is provided at its forward portion with an annular, radially outwardly extending projection 58 and an annular, radially inwardly extending groove 59.

The collar 61, of FIG. 14, is provided with an outer cylindrical surface 63, in which is formed the external circumferential groove 19, for receiving the retaining ring 40, an outer annular tapered surface 24, a chamfer or inner annular tapered surface 26 and an inner cylindrical surface 65; additionally, the collar 61 is provided at its rearward portion with an annular, radially inwardly extending projection 68 and an annular, radially outwardly extending groove 69. Similarly, the collar 71 of FIG. 16 is provided with an outer cylindrical surface 73, an outer annular tapered surface 24 and a chamfer or inner annular tapered surface 26 and an inner spherical surface 75; additionally, the collar 71 is provided at its rearward portion with an annular, radially inwardly extending projection 78 and an annular, radially outwardly extending groove 79. It will be noted and understood that the collars 61 and 71 are made of a suitably flexible material and are split radially, or circumferentially, as indicated respectively at 64 and 74 to permit the collars to be expanded radially outwardly or circumferentially for assembly with the primary segment 51.

Prior to assembly with the ball-shaped or spherical femoral head 16 of the femoral component 12 (FIG. 1), the primary bearing segment 51 and either of the collar 61 of FIG. 14, or the collar 71 of FIG. 16, are assembled together in a sub-assembly to facilitate handling by the surgeon for the reasons noted above. More particularly, and as illustrated in FIG. 17 with regard to collar 61 (it will be understood that the collar 71 is assembled in the same manner), the collar 61 is expanded radially outwardly or circumferentially (preferably prior to the operation and prior to sterilization or packaging) to permit the projection 68 to pass over the projection 58, and upon the collar 61 contracting, the projection 68 is received within the groove 59 and the projection 58 is received within the groove 69 whereupon the primary bearing segment 51 and collar 61 are assembled into a sub-assembly as illustrated in FIG. 18.

It will be further noted and understood that upon the split bearing insert 20E including the collar 61, the flexible retaining ring 40 is also utilized and is received within the groove 19 as illustrated in FIGS. 17 and 18; in this embodiment, the retaining ring 40 assists in maintaining the primary bearing segment 51 and the collar 61 in a sub-assembly. However, it will be understood by those skilled in the art that it is within the present invention to provide a collar which is made of a more rigid material wherein the collar is comprised of a plurality of annular segments provided in their outer surface with a groove (e.g. groove 19) for receiving the flexible retaining ring 40 which maintains the annular segments together and on the primary bearing segment 51 to provide the bearing insert sub-assembly.

Thus, as illustrated in FIG. 18, it will be understood that upon either the collar 61 or the collar 71 being assembled to the primary bearing segment 51, the same outside configuration of the bearing insert embodiments described above is provided. Similarly, it will be understood that the inner spherical surface 55 of the primary bearing segment 51 and either the inner spherical surface 65 of the collar 61 or the inner spherical surface 75 of the collar 71 cooperatively provide a spherical cavity or seat preferably closely matching and for receiving the spherical femoral head 16 (FIG. 1) of the femoral component 12 (FIG. 1), such spherical seat being identified in FIG. 18 as seat 57E. It will be further understood that as with regard to the above-described embodiments of the split bearing insert of the present invention, that the opening to the spherical seat 57E provided by the chamfer 26 of the collars 61 and 71 is smaller than the diameter of the spherical head 16 of FIG. 1.

Assembly of the split bearing insert 20E with the spherical femoral head 16 of the femoral component 12 (FIG. 1), will now be described with reference to FIGS. 19(a) through 19(d), with the split bearing insert 20E illustrated therein comprised of the collar 61 of FIG. 14; however, it will be understood that upon the split bearing insert 20E including the collar 71 of FIG. 16 such assembly is made in a similar manner.

As illustrated in FIG. 19(a), upon the chamfer 26 of the collar 61 (FIG. 14) being forced into engagement with the spherical femoral head 16 (manual force supplied by the operating) surgeon being more than sufficient and such force being indicated by the arrows 81 and 83) the collar 61 expands radially outwardly or circumferentially at the split 64 and against the action of the retaining ring 40, as illustrated in FIG. 19(b), to permit the collar 61 to pass over the spherical femoral head 16 and permit the spherical femoral head 16 to be seated within the spherical cavity or seat 57E (FIG. 18) of the split bearing; the acetabular cup 30, as with regard to the split bearing insert 20 described above and illustrated in FIGS. 6(a) and 6(b), is then pushed over the split bearing insert 20E to cause the chamfer or inner annular tapered surface 35 of the acetabular cup 30, FIG. 6(a), to engage the retaining ring 40 and compress it radially inwardly completely within the external circumferential groove 19 provided on the collar 61 thereby allowing the acetabular cup 30 to pass over the retaining ring 40 whereupon the split bearing insert 20E with the spherical femoral head 16 seated therein are both completely seated within the spherical cavity or seat 38 (FIG. 3) and the elements comprising this embodiment of the present invention occupy the position shown in cross section in FIG. 20 with the retaining ring 40 residing partially within the external groove 19 of the collar 61 and residing partially within the internal groove of the acetabular cup 30 whereby the retaining ring 40 maintains the bearing insert 20E within the acetabular cup 30 during rotation of the joint.

Upon the collar 71 of FIG. 16 being assembled to the primary bearing segment 51 to provide the above-noted sub-assembly, and upon this sub-assembly being assembled to the spherical femoral head 16 in the manner illustrated in FIGS. 19(a) through 19(d) with regard to collar 61, the ridge 43 engages the internal groove 37 of the acetabular cup 30 whereby the acetabular cup is retained on and over the split bearing insert and separation between the bearing insert (with the femoral head seated therein) and the acetabular cup is prevented during joint rotation. It will be understood that as in the split bearing insert 20D, FIG. 12(d), a clearance, e.g. clearance 46 of FIG. 12(d), must be provided between the inner spherical surface 75 and the spherical femoral head 16 to allow contraction of the collar 71 as the ridge 43 enters the cylindrical surface 33 of the acetabular cup 30 (FIG. 3).

Disassembly of the bearing insert 20E, whether in subassembly with the collar 61 or the collar 71, may be provided with the release ring 46 described above with regard to the bearing insert 20 utilizing the retaining ring 40 or with regard to the bearing insert 20D utilizing the circumferential ridge 43.

In the embodiment of the present invention illustrated in FIG. 20, the overlap angle γ is approximately 30° and the rotational or pivotal motion provided is approximately 60°.

Referring again generally to the present invention, it will be understood that the alternate embodiments of the split bearing insert shown in FIGS. 2, 9, 10, 11 and 12 are split along a plane (e.g. plane coincident with the center line C/L of FIG. 2) oriented perpendicular with respect to the plane 85-85, FIG. 2, defined by the opening to the spherical cavity or seat 27 provided by the chamfer 26, and that the low-friction split bearing insert alternate embodiment 20E of FIGS. 13 and 14 is split along a plane illustrated by line 87-87, FIG. 13, which is oriented parallel to the plane indicated by the line 85-85 defined by the opening to the spherical cavity or seat 57E provided by the chamfer 26 of the collar 61, FIG. 14; in each embodiment, the split bearing insert is comprised of a plurality of bearing segments and a plurality of split bearing segments.

Referring generally to all of the various embodiments of the improved bearing inserts of the present invention, it will be noted by those skilled in the art that in the embodiments of FIGS. 2, 9, 10 and 18 the respective bearing inserts are comprised of a plurality of bearing segments that are in fact physically distinct and that the bearing inserts of FIGS. 11 and 12(a)-(d) are comprised of a plurality of bearing segments that are physically distinct except for integral flexible members C and D, respectively, provided at their rearward portions; hence the expression "comprised of a plurality of 'substantially' physically distinct bearing segments" is used in the appended claims to describe both the bearing insert embodiments where the bearing segments are in fact physically distinct and the bearing insert embodiments when the bearing segments are physically distinct except for the integral flexible members C and D.

Referring now generally to the above specifically described alternate embodiments of the improved spherical joint of the present invehtion, it will be noted that such joint provides a large, or substantial, overlap angle γ, as illustrated in FIGS. 6(b) and 20, resulting in great dislocation resistance with very low assembly and disassembly forces required. For outward radial expansion of the various alternate embodiments of the split bearing insert to permit insertion of the ball-shaped head, e.g. spherical femoral head into the spherical seat or cavity provided by the various alternate embodiments of the split bearing insert only a thin retaining ring needs to be flexed or expanded radially outwardly, or a relatively thin integrally formed spherical plastic bridge, or opposed tabs, or a flexible pin, needs to be flexed, or a radially split annular collar needs to be expanded radially outwardly. Similarly, acetabular cup 30 can be easily assembled and disassembled to or from the various alternate embodiments of the split bearing insert with the ball-shaped head, e.g. spherical femoral head, seated therein by a small radially inward or radially outward deflection of a thin retaining ring while great separation resistance is provided. Furthermore, in the embodiments using the retaining ring 40, since there is no deformation of the various split bearing inserts needed for either assembly operation, no axial play is introduced resulting in a well fitting split bearing insert.

The femoral component 12 and the acetabular cup 30 may be made of rigid implantable metal such as stainless steel, titanium, or cobalt chromium alloy as well as certain suitable ceramics. The various embodiments of split bearing insert may be made of any material suitable for articulation with the spherical head 16 with a sufficient strength to provide adequate dislocation and separation resistance, and in the case of the split bearing insert 20E (FIGS. 13-20) any suitable material sufficiently flexible to provide the desired function of the collars 61 and 71. A typical material found to be suitable for these split bearing inserts is ultra-high molecular weight polyethylene (UHMWPE) and suitable certain ceramics may also be satisfactorily used for those split bearing embodiments not utilizing a flexible hinge or bridge or a flexible annular collar.

Referring again to the split bearing insert 20E of FIGS. 13-20, it will be understood by those skilled in the art that the sub-assembly including the primary bearing insert 51 and either collar 61 or 71 may be disassembled from the acetabular cup 30 other than by use of the release ring 46, FIGS. 5(a)-5(c), and the radially disposed slots or grooves 39 of the acetabular cup 30, FIG. 3, e.g. the forward portions of the collars 61 and 71 adjacent the respective splits 64 and 74 may be provided with inwardly extending holes or slots into which the ends of conventional clamps typically found in the operating room may be inserted to squeeze the collar together thereby reducing the circumference of the collars at the radial split whereby either the retaining ring 40 of collar 61 or the ridge 43 of collar 71 is disengaged from the groove 37 of the acetabular cup 30 and the bearing insert 20E with the femoral head 16 seated therein may be separated from the acetabular cup 30, by manual force provided by an operating surgeon being more than sufficient.

It will be still further understood by those skilled in the art that various modifications and variations of the present invention may be made without departing from the spirit and the scope thereof.

What is claimed is:

1. An improved spherical prosthetic joint for providing three degrees of rotational movement between two bones comprising:
   (a) a first component for engaging one of two said bones and providing internally a first seat;
   (b) a second component for engaging the other of said two bones and including a neck and a spherical head;
   (c) a substantially cup shaped bearing insert having a central axis comprising:
      (i) a pair of opposed and substantially distinct clam shell-shaped bearing members separated by a plane of separation aligned substantially along said central axis and providing internally a second seat having an opening, said second seat for receiving said head and said clam shell-shaped bearing members having rearward portions,
      (ii) a hinge provided at said rearward portions about which hinge said clam shell-shaped bearing members pivot outwardly and expand to permit said head to be received into said second seat;
   (d) said bearing insert and said first component provided with cooperative retaining means for retaining said bearing insert within said first seat upon insertion of said bearing insert into said first component; and
   (e) upon said head being received within said second seat with said neck extending through said opening, said bearing insert for being received and retained within said first seat with said first component constraining said bearing members against pivoting outwardly thereby confining said head within said second seat whereby said rotational movement between said two bones is permitted, said bearing insert providing an overlap angle for preventing dislocation of said head from said bearing insert during said rotational movement.

2. An improved spherical hip prosthesis for receiving and retaining a spherical head having a neck during three degrees of rotational movement between said prosthesis and said spherical head, comprising:
   (a) a first component for engaging a hip bone and providing internally a first seat;
   (b) a substantially cup shaped bearing insert having a central axis comprising:
      (i) a pair of opposed and substantially distinct clam shell-shaped bearing members separated by a plane of separation aligned substantially along said central axis and providing internally a second seat having an opening, said second seat for receiving said spherical head and said clam shell-shaped bearing members having rearward portions,
      (ii) a hinge provided at said rearward portions about which hinge said clam shell-shaped bearing members pivot outwardly and expand to permit said spherical head to be received into said second seat;
   (c) said bearing insert and said first component provided with cooperative retaining means for retaining said bearing insert within said first seat upon insertion of said bearing insert into said first component; and
   (d) upon said head being received within said second seat with said neck extending through said opening, said bearing insert for being received and retained within said first seat with said first component constraining said bearing members against pivoting outwardly thereby confining said head within said second seat whereby said relative rotational movement is permitted, said bearing insert providing an overlap angle for preventing dislocation of said head from said bearing insert during said rotational movement.

3. An improved spherical prosthetic joint or hip prosthesis according to claim 1 or 2 wherein said hinge comprises an outwardly extending tab and an inwardly extending recess provided at the rearward portion of each of said clam shell-shaped bearing members, each tab of each bearing member for being received within the recess formed in the other of said bearing members.

4. An improved spherical prosthetic joint or hip prosthesis according to claim 1 or 2 wherein said hinge comprises a flexible pin and wherein each of said bearing members is provided at its rearward portion with an inwardly extending hole, said pin for being received within said holes.

5. An improved spherical prosthetic joint or hip prosthesis according to claim 1 or 2 wherein said hinge comprises a flexible member formed integrally with said rearward portions of said bearing members.

6. An improved spherical prosthetic joint or hip prosthesis according to claim 1 or 2 wherein said hinge also prevents shearing separation of said bearing members along said plane of separation.

7. An improved spherical prosthetic joint or hip prosthesis according to claim 1 or 2 wherein said cooperative retaining means comprise an internal groove formed in said first component and an at least partial circumferential integral ridge formed externally on each of said clam shell-shaped bearing members, said ridges for being received within said groove upon said bearing insert being received within said first seat.

8. An improved spherical prosthetic joint or hip prosthesis according to claim 1 or 2 wherein said cooperative retaining means comprise an internal groove formed in said first component, an external groove formed in each of said clam shell-shaped bearing members, and a retaining ring for being partially received in said grooves upon said bearing insert being received within said first seat.

9. An improved spherical prosthetic joint or hip prosthesis according to claim 1 or 2 further including resilient means for maintaining said clam shell-shaped bearing members together in a sub-assembly to prevent separation therebetween prior to and during assembly with said first and second components and for permitting said sub-assembly to pivot about said hinge and expand outwardly to permit said head to be inserted into said second seat.

10. An improved spherical prosthetic joint or hip prosthesis according to claim 9 wherein an external groove is formed in each of said clam shell-shaped bearing members, and wherein said resilient means comprises a retaining ring for being at least partially received in said grooves.

11. An improved spherical prosthetic joint or hip prosthesis according to claim 1 or 2 wherein each of said pair of clam shell-shaped bearing members is provided with an outer spherical surface, an outer cylindrical surface, an outer annular tapered surface, an inner spherical surface, an inner annular tapered surface, and a generally U-shaped longitudinally extending surface, said outer spherical surface merging with the inner end of the outer cylindrical surface and the outer end of the cylindrical surface terminating with the inner end of said outer annular tapered surface, said inner spherical surface terminating with the inner end of said inner annular tapered surface, the outer ends of the inner and outer annular tapered surfaces intersecting, and wherein said generally U-shaped longitudinally extending surfaces are for being placed in generally opposed relationship defining said plane of separation.

12. An improved spherical prosthetic joint or hip prosthesis according to claim 11 wherein each of said clam shell-shaped bearing members is provided with a pair of scallops contiguous with and merging into said inner annular tapered surface and said generally U-shaped longitudinally extending surface, said scallops facilitating said insertion of said head into said second seat by reducing the amount of outward expansion of said clam shell-shaped bearing members required to permit said head to pass through said opening and be inserted into and received within said second seat.

13. An improved joint or hip prosthesis according to claim 1 or 2 wherein said first component is generally semi-hemispherically shaped and is provided with outer and inner spherical surfaces, outer and inner annular tapered surfaces each having outer and inner ends, and an inner cylindrical surface having outer and inner ends, said outer spherical surface terminating at the inner end of said outer annular tapered surface, said outer and inner annular tapered surfaces merging at their outer ends, said inner end of said cylindrical surface merging with the outer end of said inner spherical surface and the outer end of said cylindrical surface merging with the inner end of said inner annular tapered surface, said inner spherical and cylindrical surfaces providing said first seat.

14. An improved prosthetic joint according to claim 8 wherein said first component is provided with at least one slot providing external access to said retaining ring whereby said retaining ring can be compressed into said external grooves to permit said bearing insert to be removed from said first component and said joint disassembled.

15. An improved spherical prosthetic joint according to claim 1 wherein said joint is a prosthetic hip joint and wherein said bones are the pelvis and femur.

16. An improved spherical prosthetic joint according to claim 1 wherein said joint is a prosthetic shoulder joint and wherein said bones are the humerus and scapula.

17. An improved hip prosthesis according to claim 2 wherein said spherical head having a neck is the spherical head and neck of a femoral stem prosthesis.

18. An improved spherical prosthetic joint or hip prosthesis according to claim 5 wherein said rearward portions of said clam shell-shaped bearing members have a predetermined thickness and wherein said flexible member comprising said hinge has a thickness less than said predetermined thickness.

* * * * *